(12) United States Patent
Zhou et al.

(10) Patent No.: US 7,382,455 B2
(45) Date of Patent: Jun. 3, 2008

(54) SPECTROPHOTOMETRIC OPTICAL SYSTEM OF MICROPLATE READER AND FILTER WHEEL THEREOF

(75) Inventors: Lihua Zhou, Shenzhen (CN); Jinhong Qiu, Shenzhen (CN)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 50 days.

(21) Appl. No.: 11/564,446

(22) Filed: Nov. 29, 2006

(65) Prior Publication Data

US 2008/0062421 A1 Mar. 13, 2008

(30) Foreign Application Priority Data

Sep. 8, 2006 (CN) .................. 2006 1 0062554

(51) Int. Cl.
*G01N 21/25* (2006.01)
(52) U.S. Cl. ...................... 356/418; 356/319
(58) Field of Classification Search ........... 356/418; 359/885
See application file for complete search history.

(56) References Cited

U.S. PATENT DOCUMENTS

| | | | | |
|---|---|---|---|---|
| 3,467,475 A | * | 9/1969 | Heinrich et al. ........... 356/418 |
| 4,030,833 A | * | 6/1977 | Barbieri .................... 356/419 |
| 4,968,148 A | | 11/1990 | Chow et al. |
| 5,784,152 A | | 7/1998 | Heffelfinger et al. |
| 2006/0160031 A1 | * | 7/2006 | Wurm et al. ............... 430/322 |

FOREIGN PATENT DOCUMENTS

| | | |
|---|---|---|
| CN | 22244227 Y | 4/1996 |
| CN | 2489340 Y | 5/2002 |
| CN | 2718570 Y | 8/2005 |
| CN | 2722278 Y | 8/2005 |
| EP | 0841577 B1 | 5/1998 |
| JP | 2000249650 | 9/2000 |
| JP | 2005055219 | 3/2005 |
| WO | 2005093471 A1 | 6/2005 |

OTHER PUBLICATIONS

Chinese Search Report for Application CN200610062554.X, filed Sep. 8, 2006.

* cited by examiner

*Primary Examiner*—Kara E Geisel
(74) *Attorney, Agent, or Firm*—Kory D. Christensen; Stoel Rives LLP

(57) ABSTRACT

A spectrophotometric optical system of a microplate reader and a filter wheel thereof are disclosed. The filter wheel comprises a pivotable wheel body, at least one narrow-band filter with a relatively long central wavelength mounted to the wheel body, and at least one narrow-band filter with a relatively short central wavelength mounted to the wheel body. The narrow-band filter with a relatively long central wavelength is provided with a diaphragm on a front surface thereof. The diaphragm is formed with a plurality of apertures. By the diaphragm attached to the front surface of the narrow-band filter with a relatively long central wavelength, an energy matching between light of longer wavelength and light of shorter wavelength may be achieved. Further, due to the uniformly distributed apertures in the diaphragm, an even light spot may be obtained.

4 Claims, 3 Drawing Sheets

SPECTROPHOTOMETRIC OPTICAL SYSTEM OF MICROPLATE READER AND FILTER WHEEL THEREOF

FIELD OF THE INVENTION

The present invention relates to a spectrophotometric optical system of a microplate reader and a filter wheel thereof

BACKGROUND OF THE INVENTION

In a spectrophotometric optical system of a microplate reader, an analog signal obtained by a photoelectric conversion should be ensured to match a range of an analog-to-digital converter (ADC) of a detection circuit. However, light of different wavelengths may carry substantively different amounts of energy. For example, an amount of energy carried by longer wavelength light might be 20 times as much as that carried by shorter wavelength light. Moreover, the light of different wavelengths share processing circuit modules, and these modules could not balance such an energy difference between lights of different wavelengths. Thus, some analog signals could not match with the range of the ADC, e.g. going beyond the limit of the range. In addition, a colorimetric element of a microplate reader generally has a plurality of colorimetric channels. In order to ensure a uniform output of the plurality of colorimetric channels, an even distributed light spot (i.e., energy of image) is required.

In order to solve the above-mentioned problems, the amounts of energy carried by light of various wavelengths in the light path shall be balanced so as to achieve substantively the same outputs. At this point, two kinds of methods might be used according to the prior art, which will be described hereinafter.

1) Adjust a gain value of an analog channel of the detection circuit rather than adjust an energy amount of the light, so as to realize an appropriate matching between the analog signal obtained via a photoelectric conversion and a range of the ADC of the detection circuit. However, as the gain value increases, a noise in the circuit also increases, thereby leading to a degraded detection accuracy.

2) Adjust energy amounts of the lights so that energy amounts of various wavelengths light are substantively the same, and thus it is no more necessary to greatly increase the gain value of the analog channel of the detection circuit. Accordingly, an excess noise due to a relatively larger gain value could be avoided and thus the detection accuracy may be improved.

For the above-mentioned latter method, the system could be incorporated with a cold mirror, an attenuator, an energy-matching type of optical filter, or a diaphragm with a center aperture. However, there are some shortcomings with any of the above-mentioned element, which will be described hereinafter.

I) For a technical solution of incorporating a cold mirror in the light path, the cold mirror will be positioned in 45 degrees with respect to an incidence light so as to turn the light travel path with 90 degrees. Thus, a suitable space room for accommodating the mirror should be designed. In addition, various parameters of the cold mirror need to be adjusted depending on a specific amount of energy carried by respective wavelength light. Accordingly, an increased cost and an enhanced failure risk will be caused.

II). For a technical solution of disposing an attenuator in front of an optical filter, the additional attenuator will notably increase a manufacture cost of the whole system.

III). For a technical solution of utilizing an energy-matching type of optical filter, it is problematic in that the process of applying a specific film to the optical filter is difficult, and moreover the optical filter with a relatively low light transmittance will has a relatively large failure risk.

IV). For a technical solution of incorporating a diaphragm with a center aperture, it is problematic in that the light spot is not even and a rim energy is low, and thus each fiber could not be assured to obtain an substantively equivalent energy.

SUMMARY OF THE INVENTION

In view of the above mentioned problems, one object of the present invention is to provide a spectrophotometric optical system of a microplate reader and a filter wheel thereof which could balance energy differences of light of different wavelengths.

Another object of the present invention is to provide a spectrophotometric optical system of a microplate reader and a filter wheel thereof which could not only balance energy differences of light of different wavelengths, but also could ensure an even light spot.

According to one aspect of the present invention, there is provided a filter wheel for a spectrophotometric optical system of a microplate reader, comprising a rotatable wheel body, at least one narrow-band filter with a relatively long central wavelength mounted to said wheel body, and at least one narrow-band filter with a relatively short central wavelength mounted to said wheel body, wherein said narrow-band filter with a relatively long central wavelength is provided with a diaphragm on a front surface thereof facing a lens of the system, said diaphragm being formed with a plurality of apertures, and wherein a ratio of a total effective area of said plurality of apertures to an effective area of said narrow-band filter with a relatively short central wavelength is equivalent to a ratio of energy amounts of shorter wavelength light passed through the narrow-band filter with a relatively short central wavelength to energy amounts of longer wavelength light passed through the narrow-band filter with a relatively long central wavelength when the diaphragm is not disposed.

In one embodiment of the present invention, one of said plurality of apertures of said diaphragm may be positioned at a center of said diaphragm and other apertures may be distributed symmetrically with respect to said center of said diaphragm.

According to another aspect of the present invention, there is provided a spectrophotometric optical system of a microplate reader, comprising a polychromatic light source, a lens, a fiber optic light guide, a calorimetric unit, a photoelectric detector, and a control and signal processing unit sequentially arranged in a light path of said system, wherein said system further includes a filter wheel positioned between said lens and said fiber optic light guide, said filter wheel comprising a rotatable wheel body, at least one narrow-band filter with a relatively long central wavelength mounted to said wheel body, and at least one narrow-band filter with a relatively short central wavelength mounted to said wheel body, and wherein said narrow-band filter with a relatively long central wavelength is provided with a diaphragm on a front surface thereof facing said lens, said diaphragm being formed with a plurality of uniformly distributed apertures, and wherein a ratio of a total effective area of said plurality of apertures to an effective area of said narrow-band filter with a relatively short central wavelength is equivalent to a ratio of energy amounts of shorter wavelength light passed through the narrow-band filter with a relatively short central wavelength to energy amounts of longer wavelength light passed through the narrow-band filter with a relatively long central wavelength when the diaphragm is not disposed.

In one embodiment of the present invention, one of said plurality of apertures of said diaphragm may be positioned at a center of said diaphragm and other apertures may be distributed symmetrically with respect to said center of said diaphragm.

By the diaphragm attached to the front surface of the narrow-band filter with a relatively long central wavelength, an energy matching between light of a longer wavelength and light of a shorter wavelength may be achieved. Further, due to the uniformly distributed apertures in the diaphragm, vignetting of a rim field may be reduced, and an even light spot may be obtained.

DETAILED DESCRIPTION OF PREFERRED EMBODIMENTS

Preferred embodiments of the invention will be described below in detail with reference to the drawings.

Figure 1:
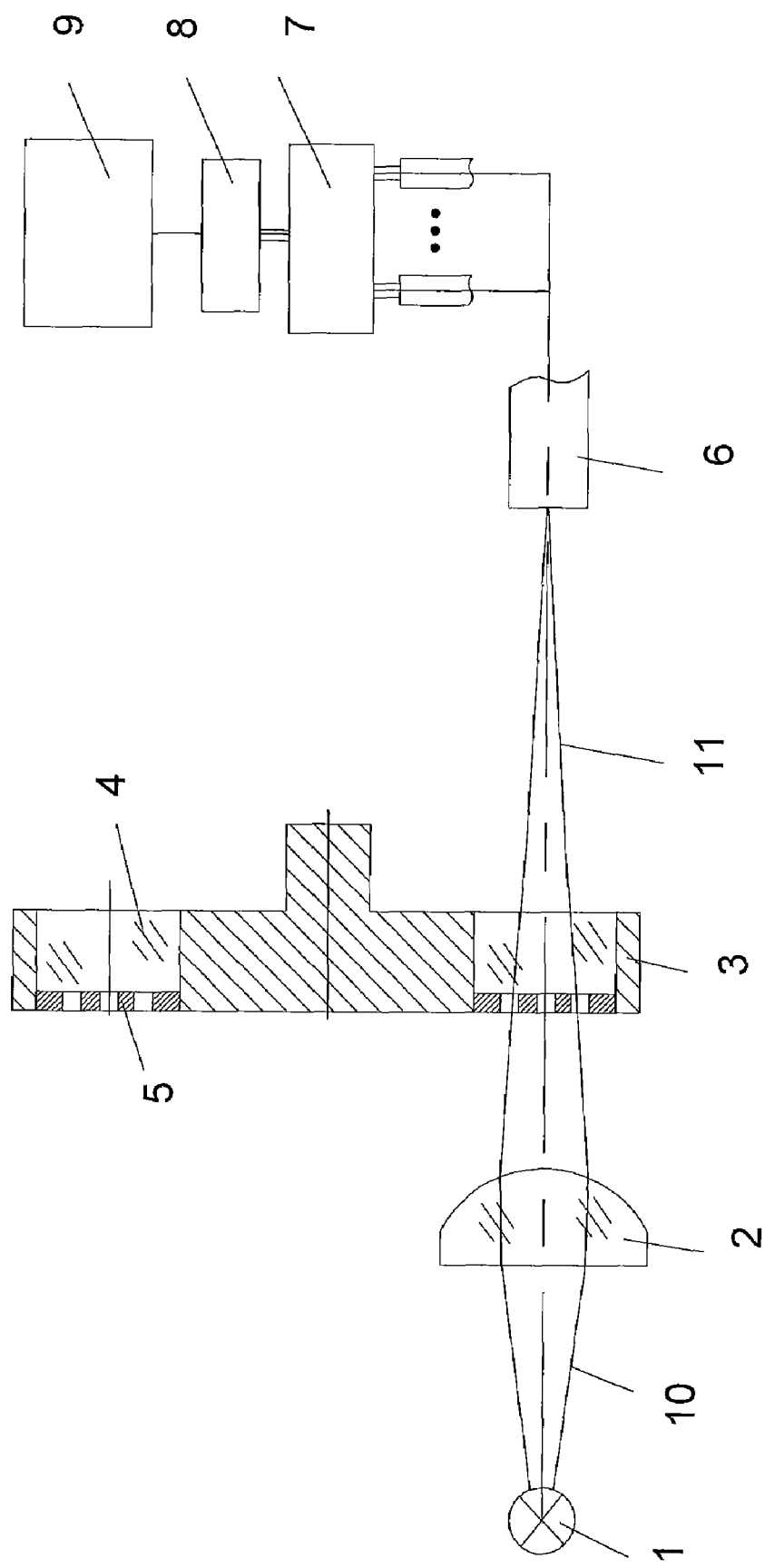
FIG. 1 is a schematic diagram illustrating a light path in a spectrophotometric optical system of a microplate reader according to the present invention.

As shown in FIG. 1, the spectrophotometric optical system of the microplate reader according to the present invention includes a polychromatic light source 1, a lens 2, a filter wheel 3, a fiber optic light guide 6, a calorimetric unit 7, a photoelectric detector 8, and a control and signal processing unit 9.

Preferably, the polychromatic light source 1 is a halogen lamp adapted to generate polychromatic light. The lens 2 is positioned between the halogen lamp 1 as the polychromatic light source and the filter wheel 3.

Figure 2:
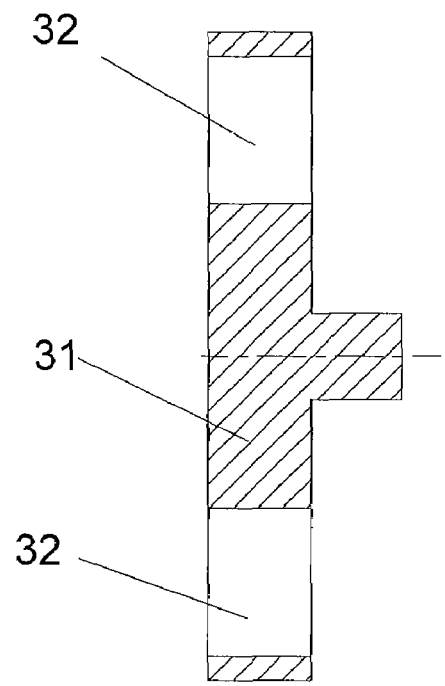
FIG. 2 is a cross-sectional view of a wheel body of a filter wheel according to the present invention.
Figure 3:
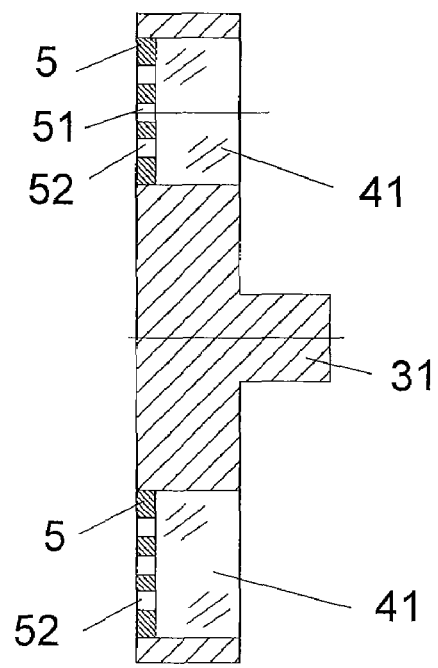
FIGS. 3 and 4 are cross-sectional views of the filter wheel according to the present invention, respectively.
Figure 4:
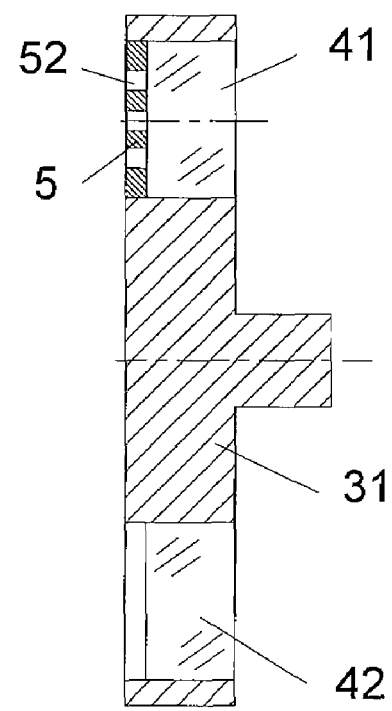

The filter wheel 3 includes a wheel body 31 as shown in FIG. 2 and at least one optical filter 4. The wheel body 31 is capable of rotating about an axis itself by means of a stepper motor (not shown). As shown in FIG. 2, the wheel body 31 is formed with a plurality of mounting holes 32 uniformly distributed in a circumferential direction thereof According to a specific desire, a plurality of optical filters 4 may be arranged. However, the number of the optical filters 4 is at most equal to that of the mounting holes 32. In addition, the optical filters 4 include a plurality of narrow-band filters 41 with relatively long central wavelengths and a plurality of narrow-band filters 42 with relatively short central wavelengths, which are all embedded into respective mounting holes 32 of the wheel body 31. The number of the filters could freely vary according to the desire.

Figure 5:
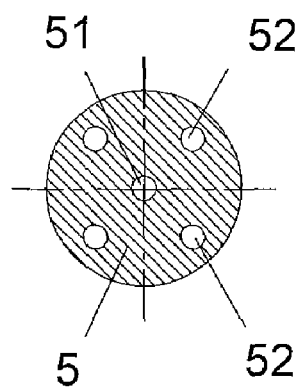
FIG. 5 is a cross-sectional view of the diaphragm according to the present invention.

The narrow-band filter 41 with a relatively long central wavelength is equipped with a diaphragm 5 at a front surface thereof facing the lens 2. The diaphragm 5 is formed with a plurality of apertures. Based on a software simulation result as well as an experiment result, preferably, one aperture 51 is positioned at a center of the diaphragm 5 and other apertures 52 are distributed symmetrically with respect to the center of the diaphragm 5, as shown in FIG. 5. According to the present invention, the narrow-band filters 42 with relatively short central wavelengths are unnecessary to be equipped with diaphragms.

The fiber optic light guide 6 has a conventional structure which is determined by a specific requirement of the spectrophotometric optical system of the microplate reader. Generally, a multiple-channel microplate reader uses a one to eight fiber bundle. In addition, the colorimetric unit 7, the photoelectric detector 8 for converting an optical signal into an electrical signal, and the control and signal processing unit 9 for pre-amplifying a received analog electrical signal, converting the analog signal into a digital one and calculating an absorbance value are all known modules, which will not be described in detail herein.

An operation of the optical detecting system according to the present invention will be described hereinafter.

Firstly, the halogen lamp 1 generates a beam of polychromatic light 10 which passes through the lens 2 and then arrives at the filter wheel 3. Before passing through respective optical filter, in the case that the filter has a relatively long wavelength, a portion of the polychromatic light might be blocked by the diaphragm 5 disposed in front of the filter. Consequently, the light beam having passed through the diaphragm gets through the optical filter 4 which just allows light of predetermined wavelengths to pass. Then the substantially monochromatic light 11 reaches a common input end (i.e. big end) of the one to more fiber optic light guide 6. Thus, the substantially monochromatic light 11 is divided into several branches and enters respective channels of the colorimetric unit 7 to undergo a colorimetric process with a certain colorimetric solution. Then, the substantially monochromatic light 11 having been processed by the colorimetric solution is converted into an electrical signal by means of the photoelectric detector 8, and the electrical signal is in turn transferred to the control and signal processing unit 9 in which the signals will be processed and an absorbance is calculated. Any of optical filters mounted on the filter wheel 3 may be freely switched into the light path by means of a rotation movement of the filter wheel 3 under a drive of the stepper motor.

In a preferred embodiment, one filter wheel is equipped with eight optical filters in total, and each narrow-band filter with a relatively long wavelength is provided with a diaphragm having five holes formed therein. Since an amount of energy carried by light of a shorter wavelength is relatively small, it is unnecessary to mount diaphragms in front of narrow-band filters with relatively short central wavelengths.

To achieve the object of the present invention, a ratio of a total effective area of the apertures of the diaphragm in front of the narrow-band filter with a relatively long central wavelength to an effective area of the narrow-band filter with a relatively short central wavelength is equal to a ratio of energy amounts of shorter wavelength light passed through the narrow-band filter with a relatively short central wavelength to energy amounts of longer wavelength light passed through the narrow-band filter with a relatively long central wavelength when the diaphragm is not disposed (i.e., a reciprocal of a ratio of energy amounts of longer wavelength light passed through the narrow-band filter with a relatively long central wavelength, when said diaphragm is not disposed, to energy amounts of shorter wavelength light passed through the narrow-band filter with a relatively short central wavelength). Herein the term of "effective area"

means an area through which lights physically pass. In an embodiment wherein the polychromatic light pass through the entire the mounting hole 32, an area S of each aperture of the diaphragm in front of the narrow-band filter with a relatively long central wavelength is calculated according to the following equation (1):

$$S = \frac{1}{n} \times \frac{A}{B} \qquad (1)$$

wherein "n" represents the number of the apertures of the diaphragm, "A" represents an area of each mounting hole, and "B" represents a ratio of the energy amounts of longer wavelength light passed through the narrow-band filter with a relatively long central wavelength, when the diaphragm is not disposed, to the energy amounts of shorter wavelength light passed through the narrow-band filter with a relatively short central wavelength. For example, in a case of a diaphragm with five apertures, the total area of the five apertures of the diaphragm in front of the narrow-band filter with a relatively long central wavelength is A/B, and each aperture has an area of A/(5B).

In the present invention, due to the diaphragm with discretely distributed apertures, vignetting of the edge rim field could be reduced, and lights in different visual fields could be balanced. The diaphragm attached to the narrow-band filter with a relatively long central wavelength weakens the energy amount of the longer wavelength light to a level equivalent to the energy amount of the shorter wavelength light, and thus an even light spot on the input end of the fiber optic light guide is achieved. Moreover, the diaphragm could be easily manufactured and has a relatively long service life as well as a convenient maintainability.

In use, the size and shape of the light spot in the optical system according to the present invention may vary in accordance with different polychromatic light sources. Accordingly, the apertures of the diaphragm could be suitably adjusted in their numbers, sizes as well as relative position relationship so as to achieve suitably attenuated light energy and an even light spot.

It will be apparent to those skilled in the art that various modifications and variations can be made in the present invention without departing from the spirit or scope of the inventions. Thus, it is intended that the present invention covers the modifications and variations of this invention provided they come within the scope of the appended claims and their equivalents.

What is claimed is:

1. A filter wheel for a spectrophotometric optical system of a microplate reader, comprising a rotatable wheel body, at least one narrow-band filter with a relatively long central wavelength mounted to said wheel body, and at least one narrow-band filter with a relatively short central wavelength mounted to said wheel body, wherein said narrow-band filter with a relatively long central wavelength is provided with a diaphragm on a front surface thereof facing a lens of the system, said diaphragm being formed with a plurality of apertures, and wherein a ratio of a total effective area of said plurality of apertures to an effective area of said narrow-band filter with a relatively short central wavelength is equivalent to a ratio of energy amounts of shorter wavelength light passed through the narrow-band filter with a relatively short central wavelength to energy amounts of longer wavelength light passed through the narrow-band filter with a relatively long central wavelength when the diaphragm is not disposed.

2. The filter wheel according to claim 1, wherein one of said plurality of apertures of said diaphragm is positioned at a center of said diaphragm and other apertures are distributed symmetrically with respect to said center of said diaphragm.

3. A spectrophotometric optical system of a microplate reader, comprising a polychromatic light source, a lens, a fiber optic light guide, a calorimetric unit, a photoelectric detector, and a control and signal processing unit sequentially arranged in a light path of said system, wherein said system further includes a filter wheel positioned between said lens and said fiber optic light guide, said filter wheel comprising a rotatable wheel body, at least one narrow-band filter with a relatively long central wavelength mounted to said wheel body, and at least one narrow-band filter with a relatively short central wavelength mounted to said wheel body, and wherein said narrow-band filter with a relatively long central wavelength is provided with a diaphragm on a front surface thereof facing said lens, said diaphragm being formed with a plurality of uniformly distributed apertures, and wherein a ratio of a total effective area of said plurality of apertures to an effective area of said narrow-band filter with a relatively short central wavelength is equivalent to a ratio of energy amounts of shorter wavelength light passed through the narrow-band filter with a relatively short central wavelength to energy amounts of longer wavelength light passed through the narrow-band filter with a relatively long central wavelength when the diaphragm is not disposed.

4. The spectrophotometric optical system of the microplate reader according to claim 3, wherein one of said plurality of apertures of said diaphragm is positioned at a center of said diaphragm and other apertures are distributed symmetrically with respect to said center of said diaphragm.

* * * * *